(12) United States Patent
Maragni et al.

(10) Patent No.: US 8,927,742 B2
(45) Date of Patent: Jan. 6, 2015

(54) PROCESS FOR PREPARING NEBIVOLOL

(75) Inventors: Paolo Maragni, Virgilio (IT); Ivan Michieletto, Venice (IT); Raffaella Volpicelli, Vicenza (IT); Giorgio Soriato, Caldiero (IT); Johnny Foletto, Arcole (IT); Livius Cotarca, Cervignano del Friuli (IT); Massimo Verzini, Caldiero (IT)

(73) Assignee: Zach Systems S.p.A., Bresso (Milano) (IT)

( * ) Notice: Subject to any disclaimer, the term of this patent is extended or adjusted under 35 U.S.C. 154(b) by 773 days.

(21) Appl. No.: 13/126,800

(22) PCT Filed: Oct. 28, 2009

(86) PCT No.: PCT/EP2009/064230
§ 371 (c)(1),
(2), (4) Date: Apr. 29, 2011

(87) PCT Pub. No.: WO2010/049455
PCT Pub. Date: May 6, 2010

(65) Prior Publication Data
US 2011/0207948 A1   Aug. 25, 2011

(30) Foreign Application Priority Data
Oct. 31, 2008 (IT) .............. MI2008A1924

(51) Int. Cl.
*C07D 311/58* (2006.01)

(52) U.S. Cl.
CPC .................................. *C07D 311/58* (2013.01)
USPC ......................................................... 549/407

(58) Field of Classification Search
USPC ......................................................... 549/407
See application file for complete search history.

(56) References Cited

U.S. PATENT DOCUMENTS

2011/0201831 A1 *   8/2011   Volpicelli et al. ............. 549/399

FOREIGN PATENT DOCUMENTS

WO   WO-2004/041805 A1 *   4/2004
WO   WO-2008/064827 A2 *   6/2008

* cited by examiner

*Primary Examiner* — T. Victor Oh
(74) *Attorney, Agent, or Firm* — Silvia Salvadori, P.C.

(57) ABSTRACT

The present invention relates to a process for preparing Nebivolol and, more particularly, to an improved method of debenzylation of a compound of formula (II) useful for preparing nebivolol endowed with high purity.

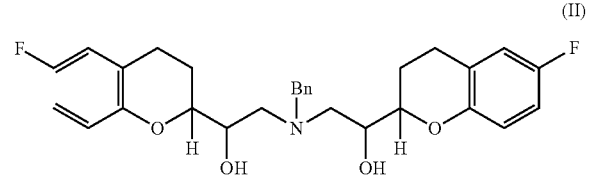

11 Claims, No Drawings

PROCESS FOR PREPARING NEBIVOLOL

This application is a U.S. national stage of PCT/EP2009/064230 files on Oct. 28, 2009 which claims priority to and the benefit of Italian Application No. MI2008A001924 filed on Oct. 31, 2008, the contents of which are incorporated herein by reference.

The present invention relates to a process for preparing Nebivolol and, more particularly, to an improved method of debenzylation of a compound of formula

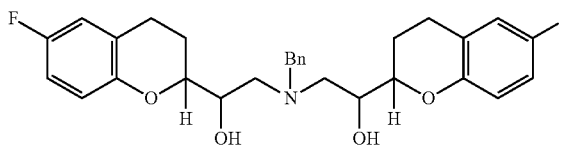

(II)

useful for preparing nebivolol endowed with high purity.

Nebivolol (hereafter, NBV), is a mixture of equal amounts of [2S [2R* [R [R*]]]] α,α'-[imino-bis (methylene)] bis [6-fluoro-chroman-2-methanol] (hereafter d-NBV) of formula (IA)

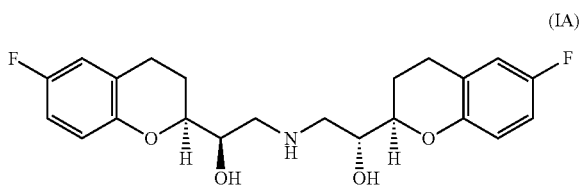 [SMILES: O[C@H](CNC[C@@H](O)[C@H]1CCc2cc(F)ccc2O1)[C@@H]1CCc2cc(F)ccc2O1]

(IA)

and its [2R [2S* [S [S*]]]] enantiomer (hereafter /-NBV) of formula (IB)

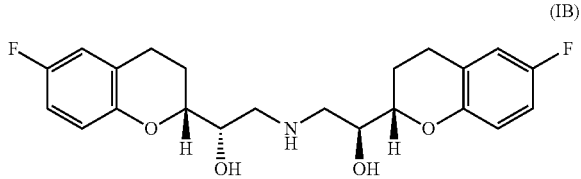 [SMILES: O[C@@H](CNC[C@H](O)[C@H]1CCc2cc(F)ccc2O1)[C@@H]1CCc2cc(F)ccc2O1]

(IB)

Nebivolol is characterized by its adrenergic β-blocking properties and is useful in treating essential hypertension. It has basic properties and may be converted into its addition salts through treatment with suitable acids. The hydrochloric acid addition salt is the marketed product.

It is known in the art that the synthesis of α,α'-[imino-bis (methylene)] bis [chroman-2-methanol] molecular structures is challenging for the skilled person because of the four asymmetric carbon atoms producing a mixture of 16 stereoisomers (in case of asymmetrical substitutions) or a mixture of 10 stereoisomers (in case of symmetrical substitutions). As apparent from the presence of symmetry in the nebivolol structure, a total of 10 stereoisomers may be generated.

Literature reports several processes for the preparation of nebivolol.

Patent EP 145067 (Janssen Pharmaceutica NV) describes a method of preparing NBV which comprises synthesizing diastereoisomeric mixtures of chroman epoxide derivatives. Said epoxide derivatives represent the key intermediates of the process which are suitably combined to give a compound of formula

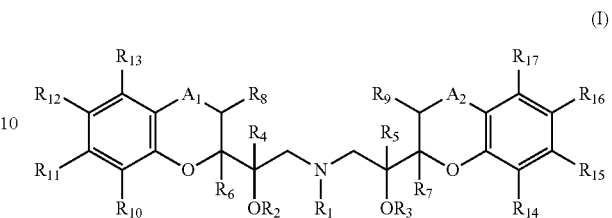

(I)

wherein $R_1$ is hydrogen, $C_{1-6}$ alkyl, aryl, aryl-$C_{1-6}$-alkyl, $C_{1-12}$ alkylcarbonyl or arylcarbonyl.

The patent description reports that the compound of formula I wherein $R_1$ is a phenylmethyl radical can be converted into a compound of formula I wherein $R_1$ is hydrogen according to hydrogenolysis procedures known in the art. In particular, in example 23 a mixture of three parts of compound $(A^+A^+)$ α,α'-[[(phenylmethyl)imino]-bis(methylene)] bis [3,4-dehydro-2H-1-benzopyran-2-methanol] and one hundred twenty parts of methanol is hydrogenated at atmospheric pressure and at room temperature with two parts of Palladium on carbon (10%).

Patent EP 334429 (Janssen Pharmaceutica NV) describes substantially the same synthetic process reported in the previous patent and is particularly directed to the preparation of single optical isomers (R,S,S,S) and (S,R,R,R) of NBV.

In this case, the deprotection of the amine group is described as actuable through catalytic hydrogenation procedures such as Palladium or Platinum supported on carbon in a suitable solvent. In example 3, a mixture of three parts and a half of benzyl derivative and two hundred fifty parts of 2-methoxy ethanol is hydrogenated at atmospheric pressure and at room temperature with two parts of Palladium on carbon (10%).

International patent applications WO 2008/010022 (Cimex Pharma AG and University of Zurich), WO 2006/025070 (Torrent Pharmaceutical Ltd), WO 2006/016376 (Hetero Drugs Ltd.) and WO 2004/041805 (Egis Gyogyszergyar RT) describe alternative processes for preparing NBV in racemic form and/or its pure enantiomers, wherein there are provided debenzylation processes through catalytic hydrogenation according to the prior art. Basically, the benzyl group is removed by a classic hydrogenation in the presence of catalyst (Pd/C).

The co-pending international patent application WO 2008/064827 in the name of the same applicant describes a process for preparing nebivolol and in particular, a process for preparing d-nebivolol and its enantiomer l-nebivolol or salts thereof starting from 2,2-dimethyl-1,3-dioxolan-4-carbaldehyde and a Grignard reagent. Steps j/u describe the deprotection of an N-benzyl derivative of nebivolol (formula Xa or Xb) according to known techniques, preferably, through catalytic hydrogenation. The patent application further provides that molecular hydrogen may be generated in situ by using alternative sources such as formic acid, ammonium formate, phosphoric acid, cyclohexene and cyclohexadiene, under catalytic hydrogen transfer reduction conditions. Example 10 of the same patent application describes the preparation of [2S, R,2'R, α'R]-α,α'-[imino bis-methylene]bis [6-fluoro-3,4-dehydro-2H-1-benzopyran-2-methanol] in the form of formate salt from the corresponding N-benzyl derivative by treatment with ammonium formate in the presence of Pd/C (10% by weight) and methanol.

Therefore, it is known in the art that protected amino groups may be debenzylated by the use of molecular hydrogen in the presence of a transition metal-based catalyst. However, a relevant drawback associable to the use of such methods is that with some substrates, subjected to hydrogenation conditions, undesired reactions may occur that lead to the formation of reaction by-products and as a consequence, reduce the purity and the yield of the end product. For example, it is known that hydrogenolysis process of protective benzyl groups in the presence of aromatic halogen groups is not chemoselective, resulting in the achievement of dehalogenated compounds in amounts unacceptable from the industrial point of view (>1%).

An alternative method useful for the hydrogenation of organic compounds is the known catalytic hydrogenation by hydrogen transfer or CTH (catalytic transfer hydrogenation), which differs from the classic methods mentioned above in that hydrogen atoms derive from compounds identified as hydrogen donors. Said CTH may be carried out in moderate conditions and, above all, they have proved to be selective in the debenzylation of protected substrates containing, in addition, aromatic halogen groups.

However, an aspect associable to CTH methods is the fact that while they are chemoselective, they exhibit the drawback of being slow and of not leading to complete conversions and, thus, of generally being little compatible or at least little productive at industrial level. One of the possible causes is represented by the progressive poisoning of the catalyst by the amines which generate as products of the N-debenzylation reaction.

Therefore, it would be desirable to study alternative debenzylation methods, which allow to overcome the drawbacks of the processes described by the prior art.

We have now, surprisingly, found a simple and efficient method of hydrogenation of intermediates useful for preparing NBV, which foresees a CTH through the use of formic acid as hydrogen source in situ.

Therefore, a first object of the present invention is a process for the debenzylation of a compound of formula

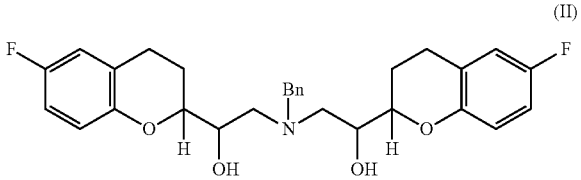 [SMILES: OC(CN(Cc1ccccc1)CC(O)C1CCc2cc(F)ccc2O1)C1CCc2cc(F)ccc2O1]

(II)

which comprises the reaction of said compound with formic acid in the presence of a Palladium-based catalyst.

In the present invention, with residue Bn it is meant a benzyl group (phenylmethyl) as known in the art.

The compound of formula II can be prepared according to known techniques, for example, according to the processes described in international patent applications and patents EP 0145067, EP0334429, WO 2006/016376, WO 2008/064827 and WO 2008/064826.

Preferably, the process object of the present invention is applied to the compound of formula II in the form of a single enantiomer RSSS (1-NBV benzyl derivative) or SRRR (d-NBV benzyl derivative) as well as, still more preferably, to the racemic mixture (±)[R*,S*,S*,S*] of the same.

The deprotection of benzyl groups through hydrogenation by hydrogen transfer is known in the art.

Generally, the reaction of a compound of formula II with formic acid in the presence of a palladium-based catalyst is carried out in the presence of one or more organic solvents optionally in admixture.

Solvents suitable for the debenzylation object of the invention are inert organic solvents such as aliphatic alcohols, ethers or esters.

Preferably, the reaction solvent is selected from methanol, ethanol, isopropanol, sec-butanol, ethyl acetate or tetrahydrofuran.

Still more preferably, sec-butanol is used as reaction solvent.

The debenzylation of the invention can also be carried out en masse.

Pd-based catalysts useful for the debenzylation object of the invention are Pd on carbon (Pd/C) either dry or wet, preferably up to about 50% w/w water. Preferably, 5% or 10% Pd/C is used.

Generally, in the reduction object of the invention, an amount of catalyst around 2-10% w/w relative to the substrate is used.

The present debenzylation of a compound of formula II with formic acid in the presence of a palladium-based catalyst is still more preferably carried out with 5% wet Pd/C (around 50% w/w water) in an amount of about 10% w/w relative to the substrate (about 5% w/w calculated on the dry catalyst).

Generally, the reaction of a compound of formula II with formic acid in the presence of a palladium-based catalyst is carried out at a temperature comprised between 25° C. and 100° C. Preferably, the reaction is carried out at around 70° C.

Generally, in the reduction object of the invention stoichiometric ratios of at least 2 moles acid/mole substrate are used. Preferably, 3 moles acid/mole substrate are used. In an aspect of the invention, the reaction of a compound of formula II with formic acid in the presence of a palladium-based catalyst is carried out by hot (70° C.±2° C.) adding formic acid to a mixture containing substrate and 5% wet Pd/C in sec-butanol. After further hot stirring for a some hours, the reaction mixture is worked up with a basic aqueous solution (for example NaOH). The catalyst is then separated from the reaction mixture through, for example, filtration on celite and product is recovered according to known techniques.

The process object of the present invention leads to the formation of an addition salt of nebivolol, namely nebivolol formate salt, which is neutralized in a basic environment, optionally in situ, to nebivolol free base.

Said NBV free base obtained from the process object of the present invention is particularly suitable, in terms of purity, for the subsequent steps of the end product synthesis.

Therefore, a further object of the present invention is a process for synthesizing nebivolol or an additional salt thereof which comprises the debenzylation of a compound of formula II with formic acid in the presence of a Palladium-based catalyst according to what reported above.

For the purposes of the present invention, it is clear that it is preferable to have as a substrate a racemic mixture of the compounds of formula II (mixture 1:1 of isomers 1 and d NBV benzyl derivative) which, suitably treated, lead to the preparation of NBV (mixture 1:1 of isomers 1 and d), in turn, converted into the end product.

So, for example, the mixture of d-NBV and 1-NBV obtained from the corresponding mixture of benzyl derivative according to the invention is treated with hydrochloric acid in the presence of an organic solvent to give the respective NBV hydrochloride salt.

Said salt may be further purified through methods known in the art such as for example crystallisation.

Hence, it is readily apparent how the reduction method object of the invention constitutes an efficient and economical synthetic alternative in the preparation of active ingredient NBV hydrochloride.

Said method, in primis, proves to be chemoselective in the presence of halogenated compounds on the aromatic ring, allowing to limit the formation of undesired by-products such as, for example, the impurity identified by a HPLC-MS assay having the structure of mono defluorinated nebivolol. Such impurity, hereinafter referred to as "de-F" nebivolol, has the general formula shown below

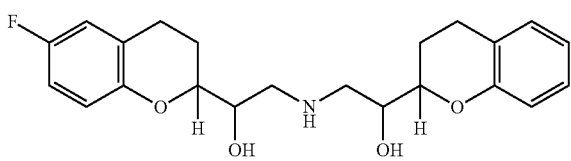

(III)

As noted above, conventional hydrogenation processes can lead to the achievement of dehalogenated compounds in large amounts (>1%) and the necessary subsequent purifications by re-crystallisation of the end product, besides being expensive in terms of time, cost and consumer materials, fail to limit the defluorinated impurities below 0.1% required by pharmaceutical standards.

As is known, it is very important to obtain a product endowed with a purity sufficient for meeting said standards. Impurities in nebivolol, as in general in any other pharmaceutical active ingredient, are absolutely undesired and in extreme cases they may even be harmful to patients treated with dosage forms containing the active ingredient.

Therefore, an important aspect of the process object of the invention is the capability of providing a highly pure end product wherein the titre of each impurity is less than 0.1% and the sum of all impurities is widely lower than 1%, making further expensive purification steps, for example by re-crystallisation, unnecessary.

Therefore, a further object of the present invention is nebivolol or an addition salt thereof, with a purity of at least 99.9% by weight.

A further object of the present invention is nebivolol or an addition salt thereof, which comprises less than 0.1% "de-F" nebivolol by weight.

A further object of the present invention is nebivolol or an addition salt thereof, which comprises less than 0.05% "de-F" nebivolol by weight.

Therefore, a further object of the present invention is a process for the synthesis of nebivolol or an addition salt thereof, with a purity of at least 99.9% by weight, which comprises a debenzylation according to what described above.

Therefore, a further object of the present invention is a process for the synthesis of nebivolol or an addition salt thereof, with less than 0.1% "de-F" nebivolol by weight, which comprises a debenzylation according to what described above.

Therefore, a further object of the present invention is a process for the synthesis of nebivolol or an addition salt thereof, with less than 0.05% "de-F" nebivolol by weight, which comprises a debenzylation according to what described above.

As mentioned above, the main drawback of CTH lies in the need of very long reaction times and, sometimes, in the difficulty in completing the reaction.

The use of formic acid according to the invention, if compared to the method of CTH in the presence of ammonium formate described in the co-pending international patent application WO 2008/064827, allows accelerating the reaction kinetic making it selective and, in the meantime, fast. Probably, the reaction mechanism that allows such acceleration may lie in the fact that unlike ammonium formate, formic acid allows the precipitation of nebivolol formate salt during the reaction through an induced crystallisation process.

The presence of formic acid, unlike ammonium formate, moreover, inhibits the catalyst poisoning process by amines (nebivolol product itself after debenzylation). Thus, from the operating point of view, it can be seen that the process we have developed compared to that described in WO2008/064827 wherein ammonium formate is hydrogen source:
  involves the use of a smaller number of hydrogen source equivalents;
  involves the use of a smaller amount of catalyst;
  involves almost quantitative conversions, high productivity and high recoveries of debenzylated product.

Moreover, nebivolol formate salt thus directly obtained, an essential intermediate for obtaining nebivolol with high purity, does not require further purifications such as preparative chromatography in formic acid environment carried out in the co-pending WO 2008/064827.

Advantages associated to the method object of the invention compared to the prior art are thus clear.

A practical embodiment of the process object of the present invention comprises the debenzylation of a compound of formula II to give nebivolol free base through a catalytic hydrogenation by hydrogen transfer with formic acid, as a hydrogen source, and in the presence of a Palladium/based catalyst.

A preferred practical embodiment of the process object of the present invention comprises reacting a racemic compound of formula II with formic acid in the presence of catalytic Pd/C and optionally in the presence of an alcoholic solvent to give nebivolol formate salt; which is neutralised to free base through a reaction with a base among which an alkaline hydroxide is preferred.

To better illustrate the invention the following examples are now given.

EXAMPLE 1

Synthesis of [2S,αR,2'R,α'R]-α,α'-[imino-bis (methylene)] bis [6-fluoro-3,4-dehydro-2H-1-benzopyran-2-methanol]

[2S,αR,2'R,α'R]-α-α'-[[(phenylmethyl)imino]bis-methylene]bis [6-fluoro-3,4-dehydro-2H-1-benzopyran-2-methanol] hydrochloride (5.3 g, 94% w/w, 9.37 mmoles) was suspended in water (20.4 g) and sec-butanol (40 g), and the heterogeneous mixture was stirred under nitrogen atmosphere at 25° C. 30% sodium hydroxide (1.5 g, 11.25 mmol) was added to the mixture and the mixture was stirred till complete dissolution of the solid. The acqueous phase was then separated and the organic alcoholic phase was recovered by washing with further solvent to give a [2S,αR,2'R,α'R]-α-α'-[[(phenylmethyl)imino] bis-methylene]bis [6-fluoro-3,4-dehydro-2H-1-benzopyran-2-methanol] free base solution in sec-butanol (57.1 g; 8.557% w/w).

A portion of this solution (52.5 g; 8.557% w/w; 9.09 mmoles) was concentrated by azeotropic distillation ($T_{ext}$=95° C.) at atmospheric pressure. The solution was then diluted with sec-butanol (17.3 g) and concentrated by azeotropic distillation under a light vacuum. Such sequence of operations was then repeated two more times obtaining a concentrated solution (24.4 g) that was then brought to volume with further sec-butanol (20.6 g). The solution was heated to 70±2° C., and Palladium/Carbon (0.526 g, Pd/C 5% wet at 57%) was added to the mixture while heating. Once the set temperature was reached, 98% formic acid (1.279 g, 27.23 mmoles) was added to the mixture in one hour by a syringe pump. The heterogeneous mixture was stirred at 70±2° C. for 3 more hours since the end of the addition and then diluted with water (19.3 g) and added with 30% sodium hydroxide (1.1 g). The mixture was kept at 70±2° C. for 15 minutes and then hot filtered under vacuum on a Celite panel, washing with sec-butanol (8.2 g) pre-heated at 70±2° C. The filtrate was kept at 60° C., then the aqueous phase was separated whereas the organic one was washed with water (2×19 g) at 60° C. The organic phase was then concentrated by vacuum distillation till a residual volume of about 40 ml. The mixture was then diluted with sec-butanol (35.3 g) and concentrated by vacuum distillation till a residual volume of about 45 ml. The organic solution was brought to 90° C., then it was cooled (in 4 hours) till 25° C. and kept at this temperature for about 16 hours.

The suspension thus obtained was diluted with a sec-butanol/water mixture (92/8 w/w) (19.9 g), heated to 80° C. and cooled (in 3 hours) to 25° C. After one more hour at 25° C., the precipitate was filtered under vacuum and the panel was washed with a sec-butanol/water mixture (95/5 w/w) (5.4 g). The precipitate was dried under vacuum at 25° C. to give the desired product (S,R,R,R)-Nebivolol as white solid (2.70 g, molar yield 71%; titre w/w HPLC=97.0%; purity HPLC=99.7% Area).

EXAMPLE 2

Synthesis of [2R,αS,2'S, α'S]-α,α'-[imino-bis (methylene)] bis [6-fluoro-3,4-dehydro-2H-1-benzopyran-2-methanol]

[2R,αS,2'S,αS]-α-α'-[[(phenylmethyl)imino]bis-methylene]bis [6-fluoro-3,4-dehydro-2H-1-benzopyran-2-methanol] hydrochloride (3.0 g, 5.64 mmoles) was suspended in water (12.2 g) and sec-butanol (24.1 g), and the heterogeneous mixture was mechanically stirred under nitrogen atmosphere at 25° C. Sodium hydroxide (0.96 g of 30% w/w aqueous solution) was added to the mixture and the mixture was stirred till complete dissolution of the solid. The aqueous phase was then separated and the organic alcoholic phase was diluted with s-butanol (15.7 g) and then subjected to azeotropic distillation under vacuum (0.04 bar). The distillation was interrupted and the mixture was brought to volume with s-butanol (23.4 g). The distillation was resumed and, at the end of the operation, the mixture was diluted with s-butanol (13.8 g) to give about 9% solution (w/w) of [2R,αS,2'S,α'S]-α-α'-[[(phenylmethyl)imino]bis-methylene]bis[6-fluoro-3,4-dehydro-2H-1-benzopyran-2-methanol] base.

The solution was heated to 70±2° C., and Palladium/Carbon (0.33 g, Pd/C 5% wet at 57%) was added to the mixture while heating. Once the set temperature was reached, a solution of formic acid (0.79 g, 16.91 mmol) and s-butanol (0.79 g) was added to the mixture in one hour by a syringe pump. The heterogeneous mixture was then mechanically stirred for 3 more hours since the end of the addition and then diluted with demi water (11.5 g), sodium hydroxide (0.88 g of a 30% w/w aqueous solution) and finally s-butanol (7.8 g). The mixture was hot filtered under vacuum on a Celite panel (1.6 g) and the panel was washed with s-butanol (12.2 g) preheated to 70±2° C. The aqueous phase was separated and stored while the organic was washed with an aqueous solution saturated with sodium bicarbonate (15.95 g) at 70±2° C. and with demi water (15.2 g) at 70±2° C. The organic phase and the initial aqueous phase at 60° C. were then combined and the biphasic mixture was diluted with demi water (15.2 g). The aqueous washing was discharged and the organic phase was subjected to distillation (P=0.03 bar; Tint=27° C.). The volume was reduced by 25% and distillation was interrupted. The temperature was set to 70±2° C. and then brought to 0° C. in 6 hours. After 10 more hours at 0° C., the precipitate was filtered under vacuum and the panel was washed with s-butanol (8.0 g). The precipitate was dried under vacuum at 60° C. to give the desired product (R,S,S,S)-Nebivolol) as white solid (1.63 g, molar yield 67%; titre w/w HPLC=94.3%; purity HPLC=99.6% Area).

EXAMPLE 3

Synthesis of (±)[R*,S*,S*,S]-α,α'-[imino-bis (methylene)] bis [6-fluoro-3,4-dehydro-2H-1-benzopyran-2-methanol]

(±)[R*,S*,S*,S*] α,α'-[(phenylmethyl)imino-bis(methylene)] bis [6-fluoro-3,4-dehydro-2H-1-benzopyran-2-methanol] (530 g; 1.07 moles) and Pd/C 5% wet at 50% (52.3 g) in sec-butanol (4970 g) were charged into a reactor. A formic acid solution (98%) (150.7 g; 3.21 moles) in sec-butanol (151 g) was added to the mixture heated to 70±2° C. in about 1 hour. The reaction mixture was kept under stirring at 70±2° C. for about 2 hours, at the end a solution consisting of NaOH 30% (225 g) in water (1900 g) was added and it was kept under stirring at 70±2° C. till dissolution of the suspension. The mixture was hot filtered on a celite panel washing with sec-butanol (726 g) and then toluene (530 g) was added. The biphasic mixture was kept at 70±2° C., then the aqueous phase was separated and the resulting organic phase was washed with an aqueous bicarbonate solution (180 g dissolved in 2400 g water) and then with water (2280 g). The organic solution was distilled under vacuum multiple times reintegrating the concentrated phase with fresh sec-butanol. The final organic phase (about 8000 ml) was heated to 85-90° C. till complete solubilization and then gradually cooled to 20° C. obtaining the product precipitation.

The solid was isolated by filtration and dried in oven under vacuum at 50° C. to give the desired product as white solid (380 g, molar yield 87.6%; titre w/w HPLC≥99%; purity HPLC≥99% Area).

EXAMPLE 4

Synthesis of (±)[R*,S*,S*,S*]-α,α'-[imino-bis (methylene)] bis [6-fluoro-3,4-dehydro-2H-1-benzopyran-2-methanol] hydrochloride (±)[R*,S*,S*,S*] α,α'-[imino-bis (methylene)] bis [6-fluoro-3,4-dehydro-2H-1-benzopyran-2-methanol] (380 g; 0.937 moles), sec-butanol (4195 g) and water (306 g) were charged into a reactor. HCl 31% (134.4 g; 1.14 moles) was added to the mixture under stirring and heated to 70±2° C. The mixture was heated to 70±2° C. for 2 hours, cooled to 20±2° C. and kept at this temperature for at least 3 hours by obtaining the product precipitation. The solid was isolated by filtration washing with sec-butanol (422 g) and dried in oven under vacuum at 60° C. to give the desired product as white solid (400.5 g; molar yield 96.7%; titre w/w HPLC≥99% (dry product); purity HPLC≥99% Area); typical purity HPLC profile: sum of impurities=0.06% w/w; "de-F" nebivolol=0.04% w/w.

$^1$H-NMR (400 MHz; MeOD) δ (ppm): 6.85-6.77 (m, 6H), 4.15-4.11 (m, 1H), 4.07-4.01 (m, 2H), 3.97-3.92 (m, 1H), 3.56-3.25 (m, 4H), 2.99-2.80 (m, 4H), 2.30-2.24 (m, 1H), 2.07-1.92 (m, 2H), 1.86-1.76 (m, 1H).

MS (ESI): m/z ([M+H]$^+$)=406.2

P.F.=225.6-226.8° C.

EXAMPLE 5

Comparison with Prior Art: N-debenzylation by Conventional Catalytic Hydrogenation Synthesis of (±)[R*,S*,S*,S*]-α,α'-[imino-bis (methylene)] bis [61-fluoro-3,4-dehydro-2H-1-benzopyran-2-methanol]

(±)[R*,S*,S*,S*] α,α'-[(phenylmethyl)imino-bis (methylene)] bis [6-fluoro-3,4-dehydro-2H-1-benzopyran-2-methanol] (18.82 g; 0.038 moles), sec-butanol (220 ml) and Pd/C 5% wet at 50% (3 g) were charged in autoclave. The mixture was heated to 80° C. and the autoclave was pressurised with hydrogen (p=4 bar). The mixture was kept under stirring in the conditions mentioned above for 17 hours and was then hot filtered on a celite panel washing with hot sec-butanol (150 ml) (using buchner lined with $t_{timer}$=85° C.). The solution was brought to room temperature to trigger the precipitation, the mixture thus obtained was kept under stirring at 15° C. for about 2 hours to complete the product precipitation.

The solid was isolated by filtration, washing with cold sec-butanol (50 ml) and dried in oven under vacuum at 35° C. to give the desired product as white solid (12.9 g; molar yield 83.7%); purity profile HPLC: "de-F" nebivolol=2.09% w/w.

Hence, it results readily apparent how the use of a conventional catalytic hydrogenation method in order to carry out a debenzylation according to the invention, entails the formation of a high percentage (>2%) of defluorinated by-product, "de-F" nebivolol, and the consequent drawbacks associated to subsequent product purifications described above.

EXAMPLE 6

Comparison with prior art: N-debenzylation by CTH according to International patent application WO 2008/064827, Example 10; isolation of Nebivolol free base and formation of Nebivolol hydrochloride has been carried out by following methods described in Examples 3 (part) and 4 above.

Part A: synthesis of (±)[R*,S*,S*,S*]-α,α'-[imino-bis (methylene)] bis [6-fluoro-3,4-dihydro-2H-1-benzopyran-2-methanol]

(±)[R*,S*,S*,S*]-α,α'-[(phenylmethyl)imino-bis (methylene)] bis [6-fluoro-3,4-dihydro-2H-1-benzopyran-2-methanol] (5.0 g; 0.0101 mol) was dissolved in methanol (343.9 g). Ammonium formate (4.8 g; 0.0761 mol) was added to the reaction mixture followed by catalytic Palladium on carbon 5 wt. % wet (contains ~50% water) (0.5 g). The reaction mixture was heated at reflux (about 65° C.) under stirring for about 11 hours then cooled to 45° C. filtered on a celite pad, washing with methanol, and finally concentrated under vacuum. The crude residue (6.2 g) was diluted with 2-butanol (65.2 g) then a solution of aq. 30% sodium hydroxide (2.0 g) and water (29.8 g) was added under stirring. The resulting suspension was heated to 70±2° C. until complete dissolution obtaining a clear two-phase mixture. The aqueous layer was separated and the resulting organic phase was washed with aq. sodium hydrogen carbonate (1.7 g dissolved in 22.6 g of water) and then with water (2×21.5 g). Toluene (5.0 g) was also added to improve the aqueous-organic separation. The organic phase was concentrated two-times under reduced pressure while adding fresh 2-butanol (total 32.9 g) to the resulting residues. The final organic solution (about 60 ml) was further diluted with 2-butanol (9.5 g) heated to 85-90° C. until complete dissolution and then gradually cooled to 20° C. obtaining the product precipitation. The solid was isolated by filtration, washing with 2-butanol (3×2.7 g), and dried under vacuum at 60° C. to give the title compound as a white solid (3.5 g, 96.6% w/w assay (HPLC); 82.6% molar yield). Purity Profile (HPLC): Sum of Impurities=0.284% w/w; Max Single Impurity ("de-F" Nebivolol)=0.196% w/w.

Part B: synthesis of (±)[R*,S*,S*,S*]-α,α'-[imino-bis (methylene)] bis [6-fluoro-3,4-dihydro-2H-1-benzopyran-2-methanol] hydrochloride (±)[R*,S*,S*,S*]-α,α'-[imino-bis (methylene)] bis [6-fluoro-3,4-dihydro-2H-1-benzopyran-2-methanol] (3.106 g; 96.6% w/w; 0.00740 mol) was dissolved in a mixture of 2-butanol (33.1 g) and water (2.0 g). Aq. conc. (about 31%) hydrochloric acid (1.1 g; 0.00903 mol) was added to the solution under stirring at 70±2° C. The resulting mixture was heated at 70±2° C. for 2 hours, then cooled to 20±2° C. over 2 hours and maintained at this temperature for further 2 hours obtaining the product precipitation. The solid was isolated by filtration, washing with 2-butanol (2×2 g), and dried under vacuum at 60° C. to give the title compound as a white solid (3.1 g, 98.3% w/w assay (HPLC); 93.2% molar yield). Purity Profile (HPLC): Sum of Impurities=0.224% w/w; Max Single Impurity ("de-F" Nebivolol)=0.178% w/w.

Hence, it results readily apparent how the N-debenzylation process by CTH described in International patent application WO 2008/064827, Example 10, besides being very slow (11 hours at reflux temperature), using a larger amount of catalyst and hydrogen source equivalents and not leading to quantitative conversion; it entails the formation of undesired by-product, "de-F" nebivolol (>0.1%), proving to be not sufficiently chemoselective.

On the contrary, starting from the same intermediate, (±) [R*,S*,S*,S*]-α,α'-[(phenylmethyl)imino-bis (methylene)] bis [6-fluoro-3,4-dihydro-2H-1-benzopyran-2-methanol], used in Part A above (batch EP109) and following the procedure described in Examples 3 and 4 of the present invention (N-debenzylation, isolation of NBV free base and hydrochloride formation), we have obtained highly pure NBV hydrochloride (Titre w/w HPLC=100.0%; Purity Profile (HPLC): Sum of Impurities=0.0272% w/w; Max Single Impurity ("de-F" Nebivolol)=0.0207% w/w).

The invention claimed is:

1. A process for the debenzylation of a compound of formula

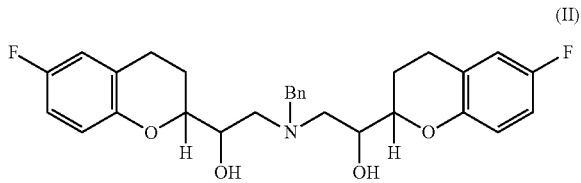 [SMILES: OC(CN(Cc1ccccc1)CC(O)C1CCc2cc(F)ccc2O1)C1CCc2cc(F)ccc2O1]

(II)

which comprises reacting said compound with formic acid in the presence of a Palladium based catalyst, wherein Bn is a benzyl group and wherein the debenzylation is carried out in the presence of sec-butanol.

2. A process according to claim 1 wherein the catalyst is Pd/C.

3. A process according to claim 2 wherein the catalyst is a wet-type Pd/C.

4. A process according to claim 2 wherein the catalyst is 5% by weight Pd/C.

5. A process according to claim 1 wherein the catalyst is used in an amount comprised from 2-10% by weight compared to the substrate.

6. A process according to claim 1 wherein the debenzylation is carried out at a temperature around 70° C.

7. A process according to claim 1 wherein the molar ratio formic acid/substrate is 3:1.

8. A process for the synthesis of nebivolol or an addition salt thereof which comprises debenzylating a compound of formula II with formic acid in the presence of a Palladium based catalyst according to claim 1.

9. A process according to claim 1, wherein a compound of formula II is present in the form of a racemic mixture (±)[R*, S*,S*,S*].

10. A process for the synthesis of nebivolol or an addition salt thereof with a purity of at least 99.9% by weight, which comprises a debenzylation according to claim 1.

11. A process for the synthesis of nebivolol or an addition salt thereof containing less than 0.1% "de-F" nebivolol by weight, which comprises a debenzylation according to claim 1.

* * * * *